(12) United States Patent
Bercovici et al.

(10) Patent No.: US 10,890,559 B2
(45) Date of Patent: Jan. 12, 2021

(54) METHOD AND DEVICE FOR ACCELERATED SURFACE-BASED REACTIONS

(71) Applicant: TECHNION RESEARCH AND DEVELOPMENT FOUNDTION LTD., Technion (IL)

(72) Inventors: Moran Bercovici, Haifa (IL); Merav Karsenty, Jerusalem (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 396 days.

(21) Appl. No.: 15/100,134

(22) PCT Filed: Nov. 28, 2014

(86) PCT No.: PCT/IL2014/051035
§ 371 (c)(1),
(2) Date: May 27, 2016

(87) PCT Pub. No.: WO2015/079446
PCT Pub. Date: Jun. 4, 2015

(65) Prior Publication Data
US 2017/0023523 A1    Jan. 26, 2017

Related U.S. Application Data

(60) Provisional application No. 61/910,132, filed on Nov. 29, 2013.

(51) Int. Cl.
*G01N 27/447* (2006.01)
*B01L 3/00* (2006.01)
(Continued)

(52) U.S. Cl.
CPC .... *G01N 27/44769* (2013.01); *B01L 3/50273* (2013.01); *G01N 27/44721* (2013.01);
(Continued)

(58) Field of Classification Search
CPC .......... G01N 27/44721–44791; G01N 33/561; G01N 33/56911; B01L 3/50273;
(Continued)

(56) References Cited

U.S. PATENT DOCUMENTS

2002/0127740 A1    9/2002  Ho
2004/0096960 A1*   5/2004  Burd Mehta ........ C12Q 1/6874
                                                      435/287.2
(Continued)

FOREIGN PATENT DOCUMENTS

WO        0050172 A1    8/2000
WO     2004027379 A2    4/2004

OTHER PUBLICATIONS

Z. Hugh Fan, et al., Dynamic DNA Hybridization on a Chip Using Paramagnetic Beads, Anal. Chem., vol. 71, pp. 4851-4859 (1999) (Year: 1999).*

(Continued)

*Primary Examiner* — Maris R Kessel
(74) *Attorney, Agent, or Firm* — The Roy Gross Law Firm, LLC; Roy Gross

(57) ABSTRACT

An ITP-based system and a method are provided. ITP is used to focus a sample of interest and deliver a high concentration target to a pre-functionalized surface comprising immobilized probes, thus enabling rapid reaction at the sensor site.

10 Claims, 4 Drawing Sheets
Specification includes a Sequence Listing.

(51) Int. Cl.
*G01N 33/561* (2006.01)
*G01N 33/569* (2006.01)

(52) U.S. Cl.
CPC . *G01N 27/44726* (2013.01); *G01N 27/44743* (2013.01); *G01N 27/44756* (2013.01); *G01N 27/44765* (2013.01); *G01N 27/44791* (2013.01); *G01N 33/561* (2013.01); *G01N 33/56911* (2013.01); *B01L 2200/0652* (2013.01); *B01L 2300/06* (2013.01); *B01L 2300/0627* (2013.01); *B01L 2300/0645* (2013.01); *B01L 2300/0816* (2013.01); *B01L 2300/0867* (2013.01); *B01L 2300/0887* (2013.01); *B01L 2300/12* (2013.01); *B01L 2400/043* (2013.01); *B01L 2400/0421* (2013.01); *B01L 2400/0487* (2013.01)

(58) Field of Classification Search
CPC ... B01L 2200/0652; B01L 2300/06–12; B01L 2400/0421; B01L 2400/043; B01L 2400/0487
See application file for complete search history.

(56) References Cited

U.S. PATENT DOCUMENTS

| | | | | |
|---|---|---|---|---|
| 2004/0115709 | A1* | 6/2004 | Morozov | G01N 33/54333 435/6.12 |
| 2008/0000774 | A1* | 1/2008 | Park | B01F 5/0646 204/549 |
| 2010/0084271 | A1* | 4/2010 | Santiago | G01N 27/44795 204/549 |
| 2010/0224494 | A1* | 9/2010 | Chambers | B01D 57/02 204/549 |
| 2011/0036718 | A1* | 2/2011 | Jung | G01N 27/44747 204/549 |
| 2012/0160689 | A1* | 6/2012 | Utz | C07K 1/26 204/549 |
| 2012/0175258 | A1* | 7/2012 | Mariella, Jr. | G01N 27/44773 204/549 |

OTHER PUBLICATIONS

H. X. Chen, et al., Capillary electrophoresis immunoassay using magnetic beads, Electrophoresis , vol. 29, pp. 3414-3421 (Year: 2008).*
S. S. Bahga, et al., Integration of rapid DNA hybridization and capillary zone electrophoresis using bidirectional isotachophoresis, Analyst, vol. 138, pp. 87-90, first available online Oct. 15, 2012 (Year: 2012).*
L. Rashkovetsky, et al., Automated microanalysis using magnetic beads with commercial capillary electrophoretic instrumentation, Journal of Chromatography A., vol. 781, pp. 197-204 (1997).*
G. Garcia-Schwarz, et al., Rapid High-Specificity microRNA Detection Using a Two-stage Isotachophoresis Assay, Angew. Chem. Int. Ed., vol. 52, pp. 11534-11537 (2013).*
Garcia-Schwarz, Giancarlo, et al. "Integration of On-Chip Isotachophoresis and Functionalized Hydrogels for Enhanced-Sensitivity Nucleic Acid Detection", Analytical Chemistry, vol. 84, No. 15, Aug. 7, 2012, pp. 6366-6369.
Karsenty, Merav, et al., "Acceleration of Surface-Based Hybridization Reactions Using Isotachophoretic Focusing", Analytical Chemistry, vol. 86, No. 6, Mar. 18, 2014, pp. 3028-3036.
Bercovici, Moran, et al, "Rapid hybridization of nucleic acids using isotachophoresis", PNAS, Jul. 10, 2012, vol. 109, No. 28, pp. 11127-11132.
Jung, Byoungsok, et al., "On-Chip Millionfold Sample Stacking Using Transient Isotachophoresis", Analytical chemistry, vol. 78, No. 7, Apr. 1, 2016.
Bercovici, M., et al., "Rapid Detection of Urinary Tract Infections Using Isotachophoresis and Molecular Beacons", Anal. Chem. 2011, 83, 4110-4117.
Schudel, Benjamin, et al., "Multiplexed detection of nucleic acids in a combinatorial screening chip", Lab Chip, 2011, 11, 1916-1923.
Persat, Alexandre, et al., "MicroRNA Profiling by Simultaneous Selective Isotachophoresis and Hybridization with Molecular Beacons", Anal. Chem. 2011, 83, 2310-2316.

* cited by examiner

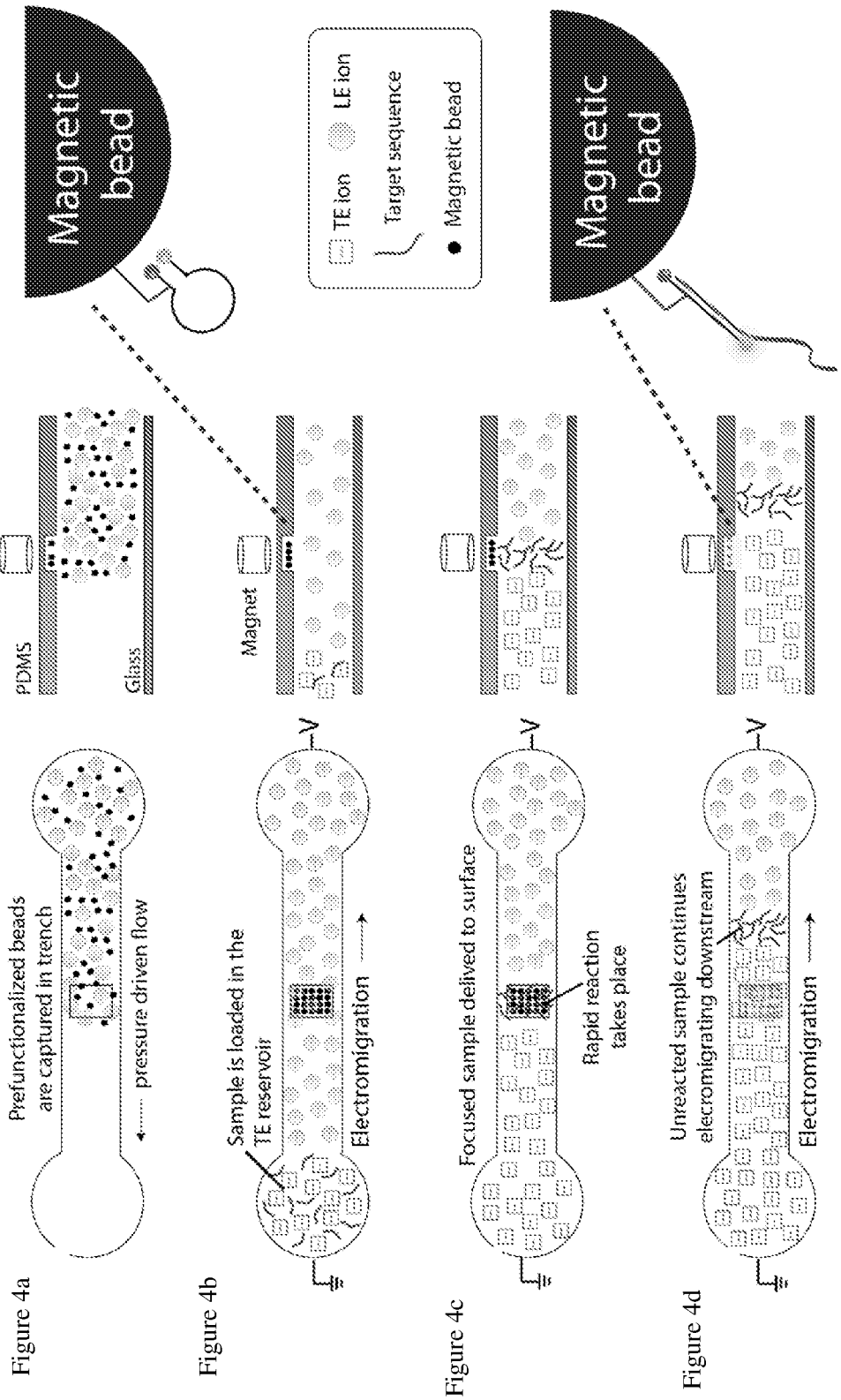

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: synthetic

<400> SEQUENCE: 1
ccggactcgt ttacrgcgtg gactaccagt ccgg                              34

<210> SEQ ID NO 2
<211> LENGTH: 22
<212> TYPE: DNA
<213> ORGANISM: Artificial Sequence
<220> FEATURE:
<223> OTHER INFORMATION: probe

<400> SEQUENCE: 2
tggtagtcca cgcygtaaac ga                                           22
```

METHOD AND DEVICE FOR ACCELERATED SURFACE-BASED REACTIONS

FIELD OF INVENTION

This invention is directed to; inter alia, a microfluidic chip and an isotachophoresis system for the detection and/or separation of proteins and nucleic acid molecules.

BACKGROUND OF THE INVENTION

Isotachophoresis ("ITP") is a variant of electrophoresis, characterized by the fact that separation is carried out in a discontinuous buffer system. Sample material to be separated is inserted between a "leading electrolyte" and a "terminating electrolyte" or mixed in any of these, the characteristic of these two buffers being that the leader has to have ions of net mobility higher than those of sample ions, while the terminator must have ions of net mobilities lower than those of sample ions. In such a system, sample components sort themselves according to decreasing mobilities from leader to terminator, in a complex pattern governed by the so-called Kohlrausch regulating function. The process has been described repeatedly, as for instance, Bier and Allgyer, Electrokinetic Separation Methods 443-69 (Elsevier/North-Holland 1979).

It is further characteristic of ITP that a steady state is eventually reached, where all components migrate at same velocity (hence the name) in sharply defined contiguous zones. Sample components can be separated in such a contiguous train of components by insertion of "spacers" with mobilities intermediary between those of the components one wishes to separate.

Surface-based biosensors are some of the most common type of sensors for biological targets such as nucleic acids and proteins. In most implementations, they are based on a "capturing probe" (e.g. an antibody or synthetic DNA sequence) which is immobilized on a surface, and to which targets specifically bind. Detection of the binding events can then be obtained in various ways, including for example fluorescence, electrochemical signals, or surface plasmon resonance (SPR). Regardless of the binding or transduction mechanism, the sensitivity of all surface biosensors is fundamentally limited by the rate at which target molecules bind to the surface. Several factors, namely diffusion, transport, and reaction rates limit hybridization or binding at low concentrations. While diffusion and transport limitation can be effectively overcome by use of devices such as mixers and flow channels, reaction rates remain a major bottleneck toward achieving rapid binding of biomolecules at low concentrations. This is because hybridization and binding typically take the form of second order reactions, with reaction time inversely proportional to the concentration of the reactants. For example, immobilized probes for nucleic acid detection are routinely utilized in microarrays, where thousands of biomarkers can be probed simultaneously. However, surface hybridization is limited by both diffusion and slow reaction kinetics compared to homogenous hybridizations, requiring long incubation times, up to several hours.

Using ITP, Jung et al. (*Anal. Chem.* 2006, 78, 2319-27) demonstrated a concentration factor of a million-fold, in less than 2 min. Bercovici et al. (*Proc. Natl. Acad. Sci.* U.S.A. 2012, 109, 11127-32) demonstrated the use of ITP for accelerating the hybridization reaction of ionic species cofocused at the ITP interface. Cofocusing target DNA with molecular beacons probes, Bercovici et al. demonstrated 10,000 fold acceleration of hybridization kinetics. Persat et al. (*Anal. Chem.* 2011, 83, 2310-16) and Bercovici et al. (*Anal. Chem.* 2011, 83, 4110-17) demonstrated the use of molecular beacons and ITP for rapid detection of miRNA and 16S rRNA, respectively. While molecular beacons are a highly attractive mechanism for detection of nucleic acids in the bulk, the majority of bioassays require surfaces to separate free probes from reacted probes and wash any nonspecific molecules. Schudel et al. (*Lab Chip* 2011, 11, 1916) recently reported the use of surface-bound molecular beacons for multiplexed detection of viral sequences. The authors reported a limit of detection of 10 nM LoD after a 1 h hybridization time and showed that the limiting step in such assays is the hybridization rate.

There is thus a growing need for methods that significantly accelerate reaction rates and lower detection time

SUMMARY OF THE INVENTION

According to a first aspect, there is provided a method of accelerating a surface-based reaction, the method comprising: (a) providing a microfluidic channel comprising at least one reaction surface, said reaction surface comprises one or more immobilized probes thereto; (b) providing a sample comprising an analyte and focusing said analyte by isotachophoresis (ITP) to an ITP focus zone; and (c) delivering said focused analyte to said probe immobilized to said reaction surface, thereby accelerating a surface-based reaction.

In one embodiment, said delivering is transversing said reaction surface. In another embodiment, said delivering is substantially modulating the electric field (e.g., stopping or reducing the voltage) on top of the reaction surface for a pre-determined period of time. In another embodiment, said delivering is applying counterflow on top of the reaction surface.

In another embodiment, said probe is selected from a nucleic acid molecule, peptide nucleic acid, peptide, protein or antibody. In another embodiment, said probe comprises a label selected from the group consisting of fluorescently labeled, chemiluminescently labeled, radioactively labeled, and colorimetrically labeled. Each possibility represents a separate embodiment of the present invention.

In another embodiment, said reaction is a hybridization reaction. In another embodiment, said reaction surface comprises a plurality of probes, such as that multiple reactions take place simultaneously.

In another embodiment, said channel has a height of 100 nm-1 mm. In another embodiment, said channel is formed by a porous material (e.g., a nitrocellulose membrane or the like).

In another embodiment, said method further comprises performing analysis of the reaction to provide information on the analyte. In another embodiment, said analyte is selected from an amino acid molecule, a nucleic acid molecule, a metabolite, a food additive, a drug constituent, a toxin, a pathogen, a heavy metal, a virus, a single celled organism, and a hormone. Each possibility represents a separate embodiment of the present invention.

In another embodiment, said sample is derived from a patient specimen, said analyte is a marker for a disease or a clinical state of a subject, and wherein said probe is capable of binding to said marker.

In another embodiment, said at least one reaction surface is coupled to a magnetic field generator, and wherein said probe is bound to a paramagnetic bead thereby immobilizing said probe to said reaction surface. In another embodiment, said at least one reaction surface comprises a groove.

According to another aspect, there is provided a microfluidic channel, comprising at least one grooved reaction site, said grooved reaction site is coupled to a magnetic field generator, said grooved reaction surface comprises a paramagnetic bead and a probe, said probe is bound to a surface of said paramagnetic bead, wherein said probe is selected from the group consisting of: a nucleic acid molecule a protein or a combination thereof, wherein said microfluidic channel is fabricated from a nonconductive substrate.

In another embodiment, said nonconductive substrate is polydimethylsiloxane (PDMS), glass or silicon. In another embodiment, said nonconductive substrate is SU8. In another embodiment, said fabricated further includes fabricated from two layers.

In another embodiment, said grooved reaction site has the dimensions of: from 2 to 80 micrometers thick, from 5 to 500 micrometers long, and from 5 to 500 micrometers wide. In another embodiment, said surface of said paramagnetic bead comprises streptavidin and said probe is biotinilated. In another embodiment, said microfluidic chip is reusable. In another embodiment, said paramagnetc bead is immobilized to said grooved reaction site. In another embodiment, said probe is selected from the group consisting of: fluorescently labeled, chemiluminescently labeled, radioactively labeled, and colorimetrically labeled. In another embodiment, said paramagnetc bead is micrometric or nanometric in size. In another embodiment, said protein is an antibody.

According to another aspect, there is provided a system comprising: (a) the microfluidic channel of the invention; and (b) a photodetector, a photomultiplier tube (PMT), a radioactive detector, a camera or any combination thereof. In another embodiment, said system further comprising a probe bound to a surface of a paramagnetic bead, wherein said probe is selected from the group consisting of: a nucleic acid molecule and a protein.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 4a-d. Schematic illustration of the assay. (4a) A microfluidic channel connecting two reservoirs is initially filled with LE and prelabeled paramagnetic beads. The solution is flown through the channel by applying pressure driven flow, and beads are trapped in the designated trench under the magnetic force of a permanent magnet placed on top of the chip. (4b) A mixture of TE and sample is injected in in the West reservoir, and an electric field is applied between the two reservoirs to initiate ITP. (4c) Highly focused target molecules are delivered to the reactive surface by ITP, and rapidly react with the probes on the surface. (4d) Unbound target molecules leave the reaction site and continue electromigrating with the ITP interface, leaving the surface embedded in TE buffer.

DETAILED DESCRIPTION OF THE INVENTION

Figure 1:
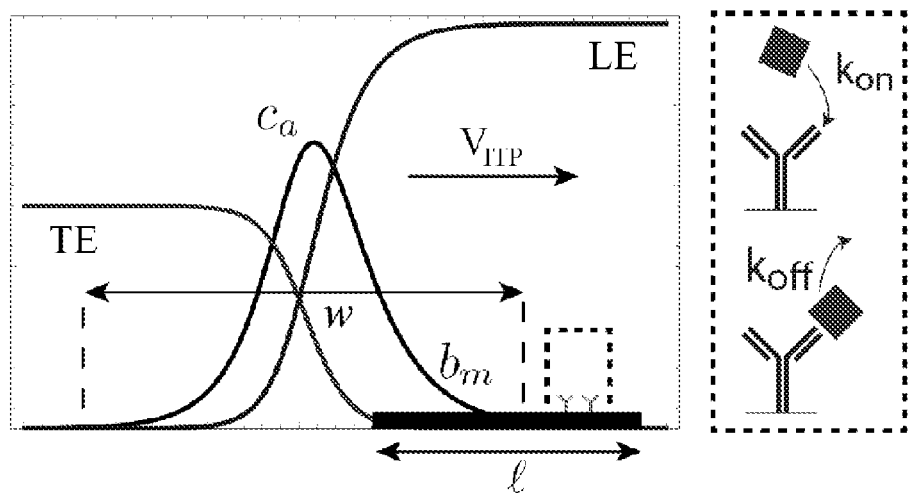
FIG. 1 is a schematic illustration of the surface hybridization assay. An analyte is focused at the sharp ITP interface between the L-ion and T-ion, which acquire constant concentration values at the far LE and TE regions, and electromigrates at a velocity $V_{ITP}$. At a distance $x_0$ from the T-ion reservoir, the analyte encounters a surface containing immobilized probes having a surface density $b_m$. As the concentrated analyte passes over the surface, its high concentration rapidly reacts with the surface probes with on- and off-rates of $k_{on}$ and $k_{off}$ respectively. The analyte overlaps with the surface for a duration of $w/V_{ITP}$, after which it continues electromigrating downstream.

The invention provides, in one embodiment, a system and a method based on ITP to focus a sample of interest and deliver a high concentration target to a pre-functionalized surface comprising immobilized probes, thus enabling rapid reaction at the sensor site. In some embodiments, the concentration of the focused analyte, to be detected specifically by the probe, is bound in space by the ITP interface, and upon reaction with the surface continues electromigrating downstream removing any contaminations or reacted sample molecules from the surface. This constitutes a one-step react-and-wash assay which can be performed in a simple channel and does not require flow control elements or moving parts.

In some embodiments, the invention provides a method of performing a surface-based reaction, the method comprising: (a) providing a microfluidic channel comprising at least one reaction surface, said reaction surface comprises one or more probes immobilized thereto; (b) performing isotachophoresis (ITP) on a sample comprising an analyte, wherein the analyte is localized to an ITP focus zone by the ITP; and (c) delivering said focused analyte to said probe immobilized to said reaction surface, thereby accelerating a surface-based reaction.

In some embodiment, the surface-based reaction of the invention is accelerated by virtue of the methods described herein. The term "accelerated" includes but is not limited to increased sensitivity of the reaction, increased limit of detection, improvement of a detected signal as well as reduced detection time.

In another embodiment, the system of the invention comprises at least one regulator selected from the group consisting of: (i) an electric field regulator; (ii) a counter-flow regulator; and (iii) a temperature regulator; or a combination thereof.

In one embodiment, said delivering is transversing said reaction surface. In another embodiment, said delivering is substantially modulating the electric field (e.g., stopping or reducing the voltage) on top of the reaction surface for a pre-determined period of time.

In another embodiment, said delivering is applying counter-flow (e.g., a flow countering the electric field) on top of the reaction surface. Said counter-flow is, in some embodiments, configured to maintain a non-migrating zone for the analyte over the reaction surface. In another embodiment, the system and method of the invention further comprise flow generating means configured to generate flow countering the electromigration of the analyte of interest. In another embodiment, the flow generating means is adjusted to equally counter the flow of the analyte. In another embodiment, the flow generating means is responsible for maintaining a stationary portion (non-migrating zone for the analyte) of the ITP over the reaction surface (and the probe immobilized thereto). In another embodiment the sum of ITP electro-migration and counter-flow generated by the flow generating means with respect to analyte within the ITP system as described herein, is substantially zero. In another embodiment, the flow generating means is electro-osmotic or pressure driven. In another embodiment, the flow generating means is a pump. In another embodiment, the flow generating means is a reciprocating pump. In another embodiment, the flow generating means is a rotary pump. In another embodiment, the flow generating means is a mechanical pump. In another embodiment, the flow generating means is an electroosmotic pump. In another embodiment, the flow generating means is the native electroosmotic flow of the channel. In another embodiment, the flow generating means is any pump known to one of skill in the art. In another embodiment, the flow generating means or pump generates a continuous flow. In another embodiment, the flow generating means or pump generates a uniform outflow. In another embodiment, the flow generating means or pump generates a uniform pressure. In another embodiment, the flow generating means or pump can be adjusted in terms of its pumping capacity, its outflow generation, its pressure generation or any combination thereof.

In another embodiment, said reaction is a hybridization reaction. In another embodiment, said surface comprises a plurality of probes.

In another embodiment, said channel has a height of 100 nm-1 mm. In another embodiment, said channel is formed on a porous hydrophilic region bounded by a fluid-impermeable barrier. In some embodiments, said porous hydrophilic region comprises: (a) a first zone configured to contain a first solution and a second zone configured to contain a second solution, said first zone and said second zone are configured to be operably connected to at least one anode and at least one cathode; (b) at least one flow channel elongated between said first zone and second zone, wherein a substantial portion of said at least one flow channel has a depth of at most 100 μm; and (c) at least one hydrophobic barrier disposed on said at least one flow channel and configured to define a contact region between a first solution and a second solution. In some embodiments, said at least one hydrophobic barrier disposed on said at least one flow channel is configured to serve as an electrokinetic repeatable interface. In some embodiments, said at least one hydrophobic barrier disposed on said at least one flow channel comprises two hydrophobic barriers forming a sample injection zone configured to suspend fluidic flow until injection of a sample to said sample injection zone.

In some embodiments, the method, microfluidic channel and/or system presented herein are applicable to any application of sample analysis and/or preparation. Biological or medical applications are of particular interest. For example, clinical screening for infection can be accomplished by obtaining a patient specimen, preferably a liquid specimen (e.g., urine sample, blood sample etc.), and performing the above described analysis, where the sample is derived from the patient specimen, and the probe is capable of binding to an analyte that is a marker for disease. Such target species that are markers for disease can include bacterial nucleotide sequences, viral RNA or DNA sequences, mitochondrial DNA sequences, micro RNA sequences, or messenger RNA sequences that encode host or pathogen proteins involved in disease, etc. The disease marker may be a nucleic acid marker used to identify one or more pathogens causing infections. This marker may be RNA or DNA and the pathogens may be bacteria, fungi, mycobacteria, prions, or viruses. Alternately, the marker may be a peptide, polypeptide, or protein associated with a disease state, a clinical or physiological state. The protein may be associated with a pathogen or with the body's response to the pathogen or disease process.

In another embodiment, said analyte is selected from an amino acid molecule, a nucleic acid molecule, a metabolite, a food additive, a drug constituent, a toxin, a pathogen, a heavy metal, a virus, a single celled organism, and a hormone. Each possibility represents a separate embodiment of the present invention.

In another embodiment, said sample is derived from a patient specimen, said analyte is a marker for a disease or a clinical state of a subject, and wherein said probe is capable of binding to said marker.

In another embodiment, said method further comprises performing analysis of the reaction to provide information on the analyte. In another embodiment, said at least one reaction surface is coupled to a magnetic field generator, and wherein said probe is bound to a paramagnetic bead thereby immobilizing said probe to said reaction surface. In another embodiment, said at least one reaction surface comprises a groove.

In some embodiments, the invention provides a novel microfluidic chip (interchangeably "microfluidic channel") where reaction surfaces in the form of trenches (interchangeably "groove") are formed for housing and maintaining paramagnetic beads carrying a probe for detecting a molecule. In some embodiments, the invention provides that the paramagnetic beads are immobilized at desired sites by an external magnetic field.

In some embodiments, the invention provides that the present microfluidic channel incorporating the components described herein was compared to standard continuous flow-based hybridization and experimentally demonstrated a 30-fold improvement in signal, and a limit of detection of 1 pM in a 3 min nucleic acid hybridization assay.

In one embodiment, the invention provides a microfluidic chip, comprising at least one grooved reaction surface, wherein the grooved reaction surface is coupled to a means for generating magnetic field, wherein the grooved reaction surface comprises a paramagnetic bead and a probe, wherein the probe is bound directly or indirectly to a surface of the paramagnetic bead, wherein the probe is selected from the group consisting of: a nucleic acid molecule and a protein, wherein the microfluidic chip is fabricated from a nonconductive substrate.

In another embodiment, the invention provides that the nonconductive substrate is a combination of substrates. In another embodiment, the invention provides that the nonconductive substrate is polydimethylsiloxane (PDMS). In another embodiment, the invention provides that the nonconductive substrate is glass. In another embodiment, the invention provides that the nonconductive substrate is SU8. In another embodiment, the invention that the microfluidic chip is fabricated or composed of at least two layers.

In another embodiment, the microfluidic chip has the following dimensions: from 10 to 80 micrometers thick, from 20 to 500 micrometers long, and from 20 to 500 micrometers wide. In another embodiment, the microfluidic chip has the following dimensions: from 20 to 300 micrometers thick, from 20 to 200 micrometers long, and from 20 to 300 micrometers wide.

In another embodiment, the paramagnetic bead is bound to the probe via a covalent bond. In another embodiment, the paramagnetic bead comprises streptavidin. In another embodiment, the probe comprises streptavidin. In another embodiment, the paramagnetic bead is biotinilated. In another embodiment, the probe is biotinilated. In another embodiment, the paramagnetic bead is bound to the probe via streptavidin-biotin.

In another embodiment, the microfluidic chip is reusable. In another embodiment, the paramagnetc bead is immobilized to the grooved reaction surface via a magnetic field. In another embodiment, the magnetic beads are confined to the grooved reaction surface or site. In another embodiment, means for inducing magnetic field are known to one of skill in the art.

In another embodiment, the grooved reaction surface or site is: from 2 to 25 micrometers deep, from 5 to 500 micrometers long, and from 5 to 500 micrometers wide. In another embodiment, the grooved reaction surface or site is: from 5 to 20 micrometers deep, from 10 to 200 micrometers long, and from 10 to 200 micrometers wide.

In another embodiment, the beads have a diameter of 2 to 200 micrometers. In another embodiment, the beads have a diameter of 5 to 100 micrometers. In another embodiment, the beads have a diameter of 10 to 100 micrometers. In another embodiment, the beads have a diameter of 40 to 900 nanometers. In another embodiment, the beads have a diameter of 40 to 400 nanometers. In another embodiment, the beads have a diameter of 200 to 600 nanometers. In another embodiment, the beads have a diameter of 600 to 900 nanometers.

In another embodiment, the probe is a protein or a nucleic acid molecule. In another embodiment, the probe is labeled. In another embodiment, the probe is fluorescently labeled, chemiluminescently labeled, radioactively labeled, or colorimetrically labeled.

In another embodiment, the present invention provides a system comprising: the microfluidic chip as described herein; an Isotachophoresis (ITP) system; and a photodetector, a photomultiplier tube (PMT), a radioactive detector, a camera or any combination thereof. In another embodiment, ITP comprises LE composed of HCl, bistris and PVP solution. In another embodiment, ITP comprises TE composed of tricine and bistris solution.

In another embodiment, the leading electrolyte (LE) buffer is chosen such that its anions have higher effective electrophoretic mobility than the anions of the trailing electrolyte (TE) buffer (Effective mobility describes the observable drift velocity of an ion and takes into account the ionization state of the ion, as described in detail by Persat et al.). In another embodiment, sample ions of intermediate effective mobility race ahead of TE ions but cannot overtake LE ions, and so they focus at the LE-TE interface (hereinafter called the "ITP interface"). In another embodiment, the LE and TE buffers are chosen such that nucleic acid molecule of interest (to be detected or separated) have a higher mobility than the TE, but cannot overspeed the LE. In another embodiment, the TE and LE buffers form regions of respectively low and high conductivity, which establish a steep electric field gradient at the ITP interface. In another embodiment, the LE buffer (or LE) has a high ionic strength. In another embodiment, the LE buffer comprises Sodium hydroxide. In another embodiment, $Mg^{2+}$ ions are used as a counter ion to promote rapid hybridization.

In another embodiment, LE comprises hydrochloric acid. In another embodiment, LE comprises 70 to 100 mM HCl. In another embodiment, LE comprises hydrochloric acid. In another embodiment, LE comprises 100 to 150 mM HCl. In another embodiment, LE comprises hydrochloric acid. In another embodiment, LE comprises 120 to 150 mM HCl. In another embodiment, LE comprises hydrochloric acid. In another embodiment, LE comprises 150 to 200 mM Bistris. In another embodiment, LE comprises 200 to 250 mM Bistris. In another embodiment, LE comprises 150 to 200 mM Bistris. 220 to 280 mM Bistris.

In another embodiment, a system as described herein further comprises a photodetector. In another embodiment, a system as described herein further comprises a photomultiplier tube (PMT). In another embodiment, a system as described herein further comprises a camera. In another embodiment, a system as described herein further comprises a radioactive probe or detector. In another embodiment, a system as described herein further comprises a calorimetric detector. In another embodiment, a system as described herein further comprises a conductivity detector.

In another embodiment, the present invention provides an ITP kit comprising the system as described herein and specific instructions for performing the method as described herein. In another embodiment, the present invention provides a kit comprising an instruction manual describing the method and/or system disclosed herein. In another embodiment, the present invention provides a kit as described herein further comprising an electrophoresis apparatus. In another embodiment, the present invention provides a kit as described herein further comprising an electrophoresis apparatus that is communicatably coupled to a central processing unit (CPU) that may operate the electrophoresis apparatus based on a predetermined set of instructions.

In another embodiment, the probe is labeled. In another embodiment, the label is Acridine orange. In another embodiment, the label is Acridine yellow. In another embodiment, the label is Alexa Fluor. In another embodiment, the label is 7-Aminoactinomycin D. In another embodiment, the label is 8-Anilinonaphthalene-1-sulfonic acid. In another embodiment, the label is an ATTO dye. In another embodiment, the label is Auramine-rhodamine stain. In another embodiment, the label is Benzanthrone. In another embodiment, the label is Bimane. In another embodiment, the label is 9,10-Bis(phenylethynyl)anthracene. In another embodiment, the label is 5,12-Bis(phenylethynyl)naphthacene. In another embodiment, the label is Bisbenzimide. In another embodiment, the label is a Blacklight paint. In another embodiment, the label is Brainbow. In another embodiment, the label is Calcein. In another embodiment, the label is Carboxyfluorescein. In another embodiment, the label is Carboxyfluorescein diacetate succinimidyl ester. In another embodiment, the label is Carboxyfluorescein succinimidyl ester. In another embodiment, the label is 1-Chloro-9,10-bis(phenylethynyl)anthracene. In another embodiment, the label is 2-Chloro-9,10-bis(phenylethynyl)anthracene. In another embodiment, the label is 2-Chloro-9,10-diphenylanthracene. In another embodiment, the label is Coumarin. In another embodiment, the label is DAPI. In another embodiment, the label is a Dark quencher. In another embodiment, the label is DiOC6. In another embodiment, the label is DyLight Fluor. In another embodiment, the label is Ethidium bromide. In another embodiment, the label is Fluo-3. In another embodiment, the label is Fluo-4. In another embodiment, the label is a FluoProbe. In another embodiment, the label is Fluorescein. In another embodiment, the label is Fluorescein isothiocyanate. In another embodiment, the label is a Fluoro-Jade stain. In another embodiment, the label is Fura-2. In another embodiment, the label is Fura-2-acetoxymethyl ester. In another embodiment, the label is GelGreen. In another embodiment, the label is GelRed. In another embodiment, the label is Green fluorescent protein. In another embodiment, the label is a Heptamethine dye. In another embodiment, the label is Hoechst stain. In another embodiment, the label is Indian yellow. In another embodiment, the label is Indo-1. In another embodiment, the label is Lucifer yellow. In another embodiment, the label is Luciferin. In another embodiment, the label is MCherry. In another embodiment, the label is Merocyanine. In another embodiment, the label is Nile blue. In another embodiment, the label is Nile red. In another embodiment, the label is an Optical brightener. In another embodiment, the label is Perylene. In another embodiment, the label is Phloxine. In another embodiment, the label is P cont. In another embodiment, the label is Phycobilin. In another embodiment, the label is Phycoerythrin. In another embodiment, the label is Phycoerythrobilin. In another embodiment, the label is Propidium iodide. In another embodiment, the label is Pyranine. In another embodiment, the label is a Rhodamine. In another embodiment, the label is RiboGreen. In another embodiment, the label is RoGFP. In another embodiment, the label is Rubrene. In another embodiment, the label is (E)-Stilbene. In another embodiment, the label is (Z)-Stilbene. In another embodiment, the label is a Sulforhodamine. In another embodiment, the label is SYBR Green I. In another embodiment, the label is Synapto-pHluorin. In another embodiment, the label is Tetraphenyl butadiene. In another embodiment, the label is Tetrasodium tris(bathophenanthroline disulfonate)ruthenium(II). In another embodiment, the label is Texas Red. In another embodiment, the label is Titan yellow. In another embodiment, the label is TSQ. In another embodiment, the label is Umbelliferone. In another embodiment, the label is Yellow fluorescent protein. In another embodiment, the label is YOYO-1. In another embodiment, the label is a chemiluminescent dye. In another embodiment, the label is a radioisotope or a radioactive dye. In another embodiment, the label is a dye that can be detected by a naked eye.

In another embodiment, the protein is a peptide. In another embodiment, the protein is a polypeptide. In another embodiment, the protein is a glycoprotein.

In another embodiment, the present method requires minimal or no sample preparation. In another embodiment, the theory behind ITP is provided in Bahga S S, Kaigala G V, Bercovici M, Santiago J G. High-sensitivity detection using isotachophoresis with variable cross-section geometry. Electrophoresis. 2011 February; 32(5):563-72; Ithurana T K, Santiago J G. Sample zone dynamics in peak mode isotachophoresis. Anal Chem. 2008 Aug. 15; 80(16):6300-7; and Isotachophoresis: Theory, Instrumentation and Applications. F. M. Everaerts, J. L. Beckers, T. P. E. M. Verheggen, Elsevier, Sep. 22, 2011, which are hereby incorporated by reference in their entirety.

In another embodiment, ITP is performed in a peak mode. In another embodiment, ITP is performed in a plateau mode. In another embodiment, "Plateau mode" refers to a wide sample-zone compared to the transition zones, i.e. the sample concentration distribution forms a plateau with blurred boundaries towards LE and TE. In another embodiment, "Peak mode" refers to a very short sample zone, where the two transition zones at both sides of the sample overlap or when the sample is entirely within the interface between LE and TE.

The simple analytical model presented herein allows prediction of the rate of surface reaction under ITP and the systems described herein, and can be used to design, and optimize such methods and assays as a function of the physical properties of the system, including buffer chemistry, applied voltage, analyte mobility, analyte concentration, probe density, and surface length. The method, model and experimental setup can be applied to various forms or surface reactions, and may serve as the basis for highly genetic analysis and immunoassays.

In some embodiments, the flow channel of said ITP used in the method and/or system of the present invention comprises a unique geometrical property, e.g., one or more narrow constrictions, to thereby enable measuring changes in the applied electric field and subsequently perform one or more pre-defined functions on the ITP interface.

Typically, a substantial change in the measured electric current or voltage indicates passage of the ITP interface through a transition region (e.g., transition between a wide and narrow section of the channel), can respectively be used for performing one or more pre-defined functions on the ITP interface. One skilled in the art will appreciate that for a constant applied voltage, the current in ITP decreases monotonically due to increase in resistance. However, a rapid and significant current drop may be observed upon entrance of the ITP interface into a constriction. In some embodiments, the significant current drop may be used for performing an action, including but not limited to, switching off the electric field. As a non limiting example, use of the ITP apparatus having a transition region can be used for delivering the concentrated ITP zone to a desired chamber, wherein upon arrival, the electric field is automatically turned off and the sample is allowed to diffuse, thereby enabling increased reaction rates. After a pre-defined time allocated for reaction, the electric field may be reestablished and the ITP interface continues electromigrating, removing any un-reacted species from the surface.

In another embodiment, the ITP apparatus of the invention comprises a small:large cross-section area ratio of 1:2-1:25. In another embodiment, said cross-section ratio is of 1:2-1:10. In another embodiment, said cross-section ratio is of 1:3-1:5. In another embodiment, said small cross-section width is in the range of 5-100 μm. In another embodiment, said small cross-section width is in the range of 10-50 μm. In another embodiment, said small cross-section has a length in the range of 20-500 μm.

A skilled artisan will appreciate that the ITP apparatus and method of the invention may apply constant voltage and detect current changes, or vice versa, apply constant current and detect voltage changes.

Theory and Principle of the Systems and Methods of the Invention

An ITP was used to focus a sample of interest and deliver a high concentration target to a pre-functionalized surface, thus enabling rapid reaction at the sensor site. The concentration of the focused analyte is bound in space by the ITP interface, and upon reaction with the surface continues electromigrating downstream removing any contaminations or reacted sample molecules from the surface. This constitutes a one-step react-and-wash assay which can be performed in a simple channel and does not require flow control elements or moving parts. We designed a novel microfluidic chip where reaction surfaces are formed by paramagnetic beads, immobilized at desired sites by an external magnetic field. Using this chip, we compared ITP-based surface hybridization to standard continuous flow-based hybridization and experimentally demonstrated a 30-fold improvement in signal, and a limit of detection of 1 pM in a 3 min nucleic acid hybridization assay. The simple analytical model we present allows prediction of the rate of surface reaction under ITP, and can be used to design, and optimize such assays as a function of the physical properties of the system, including buffer chemistry, applied voltage, analyte mobility, analyte concentration, probe density, and surface length. The method, model and experimental setup can be applied to various forms or surface reactions, and may serve as the basis for highly genetic analysis and immunoassays.

In peak mode ITP, a low concentration analyte is focused at a narrow interface between a high electrophoretic mobility leading electrolyte (LE) and low electrophoretic mobility trailing electrolyte (TE). In another embodiment, focusing is achieved by mixing sample analytes with the LE or TE buffers (typically referred to as 'infinite sample injection') or injected in an independent zone between these electrolytes (referred to 'finite sample').

In another embodiment, infinite sample injection is performed in which sample ions are mixed with the TE and continuously accumulate at the ITP interface. In another embodiment, the method and analysis is directly applied to other injection modalities. In another embodiment, as illustrated in FIG. 1, a straight microfluidic channel having a cross section area A, height h, and containing a finite segment of immobilized probes centered at a distance $x_0$ from the West (TE) reservoir, is used. The surface density of the probes was denoted $b_m$, and the length of the reactive surface as l.

FIG. 1 is a schematic illustration of the surface hybridization assay. An analyte is focused at the sharp ITP interface between the LE and TE, and electromigrates at a velocity $V_{ITP}$. At a distance $x_0$ from the TE reservoir, the analyte encounters a surface containing immobilized probes having a surface density $b_m$. As the concentrated analyte passes over the surface, its high concentration rapidly reacts with the surface probes with on- and off-rates of $k_{on}$ and $k_{off}$ respectively. The analyte overlaps with the surface for a duration of $(l+w)/V_{ITP}$, after which it continues electromigrating downstream.

The initial conditions for ITP are formed simply by filling the channel and East reservoir with LE solution, and filling the West reservoir with a mixture of TE and target molecules. Under an applied electric field, the ITP front, containing focused analyte molecules, electromigrates from West to East. The number of target molecules accumulated at the ITP interface, $N_a$, as a function of its location along the channel, x, is given by $$N_a(x) = \underbrace{\left[\left(\frac{\mu_a}{\mu_{TE}} - 1\right)\frac{\mu_{TE}}{\mu_{LE}}\frac{\mu_{Cl} - \mu_{LE}}{\mu_{Cl} - \mu_{TE}}\frac{c_{LE}}{c_{TE}^{well}}\right]}_{\eta_{TE}} A c_0 x = \eta_{TE} A c_0 x$$

(Khurana, T. K. & Santiago, J. G. Sample zone dynamics in peak mode isotachophoresis. Anal. Chem. 80, 6300-6307 (2008).).

Here, $\eta_{TE}$ is a dimensionless buffer-dependent factor which governs the rate of focusing, $\mu_a$, $\mu_{LE}$, $\mu_{TE}$, $\mu_{Cl}$ are respectively the effective electrophoretic mobilities of the analyte, LE, TE, and counterion, $c_{LE}$ is the concentration of the leading ion, $c_{TE}^{well}$ is the concentration of the TE ion in the reservoir (i.e. before adaptation), and $c_0$ is the initial concentration of the analyte in the same reservoir.

This high concentration zone steadily electromigrates down the channel and reaches the sensor surface which contains immobilized capture probes. Assuming Langmuir kinetics at the surface, the concentration of surface probes bound by target molecules follows (in dimensional form):

$$\frac{\partial b(x, t)}{\partial t} = k_{on}[b_m - b(x, t)]c_a(x, t) - k_{off}b(x, t)$$

where $k_{on}$ $M^{-1}s^{-1}s^{-1}$ and $k_{off}$ $s^{-1}$ are respectively the on- and off-rates of the reaction, $[b_m-b(x,t)]$ is the surface density of available (unbound) probes, and $c_a(x,t)$ is the target molecule concentration at the surface. Assuming an ITP velocity of 50 μm/s (typical in our experiments) and surface length of l=100 μm we obtain that the interface transverses the surface at a characteristic time of $\tau_{ITP}=(l+w)/V_{ITP}$~4 s where w is the typical width of analyte sample. At the same time, assuming a channel height of h=20 μm, and a diffusion coefficient of $D=5\cdot 10^{-9}$ $m^2/s$, the characteristic diffusion time is of order $\tau_d = h^2/D \sim 0.1$ s. Hence, while passing over the surface, target molecules at the ITP interface have sufficient opportunity to 'sample' the surface. Clearly, for higher ITP velocities or deeper channels this assumption no longer holds. Under this assumption, we may write the area averaged Nernst Planck equation for the target molecule as $$\frac{\partial c_a}{\partial t} + \frac{\partial}{\partial x}\left[(z\mu E - V_{ITP})c_a - D\frac{\partial c_a}{\partial x}\right] = \frac{1}{h}[-k_{on}c_a b + k_{off}b]$$

where, consistently with the discussion above, all $c_a$ molecules in a given cross section are available for reaction with the surface, and the 1/h factor on the right hand side transfers the surface density b to a volume concentration b/h. Notably, the continuum description of the presented equations is expected to break down below critical concentration, corresponding to one target molecule, or less, per sensor volume. For example for a typical sensor volume of 20 µm×50 µm×100 µm, equivalent to 100 pL, the critical concentration is of order $c^{crit} \sim 10$ fM.

The relative change in the concentration of the target molecule as it passes over the surface is of the order $$\frac{\Delta c_A}{c_A} \sim \frac{k_{on}b}{h}\Delta t \sim \frac{k_{on}b_m \ell}{hV_{ITP}}.$$

Taking $k_{on} \sim 10^3 - 10^4$ [M$^{-1}$s$^{-1}$], $b_m \sim 10^{12}$ [copy/cm$^2$], yields $$\frac{\Delta c_A}{c_A} \sim 10^{-3} - 10^{-2}.$$

i.e. during the relevant time scale, the amount of target bound to the surface is 0.1-1%. Furthermore, the typical length of the reactive surface (order ~10-100 µm) is significantly shorter than the typical distance from the TE reservoir to the reaction site (order ~1-10 cm), $1 x_0$. Hence, as the ITP interface passes over reactive surface, the relative change in analyte concentration due to ITP accumulation, is of order $$\frac{\Delta c_A}{c_A} \sim \frac{\ell + w}{x_0} \sim 10^{-2},$$

i.e. during $\tau_{ITP}$, the concentration of target ions increased by just 1%. Thus the target concentration profile can be assumed to have a constant number of molecules, and take the form of a translating wave of the type $$c_a(x,t) = N_a \frac{\sin(\pi L/L_a)}{AL\pi} \frac{\exp[(x - V_{ITP}t)/L_a]}{1 + [(X - v_{itp}T)/L]}$$

where the interface and analyte length scales are defined respectively as $$L^{-1} = \frac{FV_{ITP}}{RT}(\mu_T^{-1} - \mu_L^{-1}) \text{ and } L_a^{-1} = \frac{FV_{ITP}}{RT}(|z_a|\mu_T^{-1} - \mu_a^{-1}),$$

F is Faraday's constant, R is a gas constant, T is absolute temperature and $V_{ITP}$ is the velocity of the ITP interface. For convenience we consider the case of a nearly symmetric analyte, characterized by $$\mu_a \sim \mu_a^{(sym)} = \frac{2\mu_L \mu_T}{\mu_L - \mu_T}$$

and nearly Gaussian profile $c_a(x,t) = c_{max} \exp[-(x-V_{ITP}t)^2/2\sigma^2]$ where, $c_{max}$ is the peak concentration $$c_{max} = \frac{N_a}{\sqrt{2\pi} A\sigma}$$

and the variance, $\sigma$, is related to the buffer properties via (Rubin, S., Schwartz, O. & Bercovici, M. Sample distribution in peak mode isotachophoresis. Under consideration (2013)

$$\frac{1}{\sigma^2} = \frac{FV_{ITP}}{RT}\frac{1}{\mu_L}\left(\frac{2}{\mu_L} - \frac{1}{\mu_T}\right)$$

Utilizing the present equations and furthermore taking advantage of the fact that there is a negligible signal decay of hybridized molecules on time scales $\tau_{ITP}$, expressed by the fact that $\tau_{ITP} 1/k_{off} \sim 10^6$ sec, allows, where $c_a(t) = c_{max} \exp[-8(1-V_{ITP}t/w)^2]$; $0 \le t \le \tau_{ITP}$. The latter represents a signal of width $w = 4\sigma$ (enclosing 95% of the Gaussian area) over each point on the reacting surface, $$-\frac{\ell}{2} \le x \le \frac{\ell}{2},$$

between times $0 \le t \le \tau_{ITP}$.

Replacing the concentration $c_a(t)$, in Eq.(7), by its time average $$\langle c_a \rangle = \frac{1}{\tau_{ITP}} \int_0^{\tau_{ITP}} c_a(t)dt,$$

explicitly given by $$\langle c_a \rangle = \underbrace{\left[\frac{\sqrt{2\pi}}{4(1+\ell/w)}erf(\sqrt{2}(1+\ell/w))\right]}_{f} \alpha c_0 = f\alpha c_0$$

introduces negligible, relative error of an order $k_{off}\tau_{ITP}$ to b ($\tau_{ITP}$) (as may be seen by integrating directly both sides of Eq.(7)) yet leads towards the following simpler reaction equation $$\frac{db(t)}{dt} = \frac{b_m}{\tau_{on}} - \frac{b(t)}{\tau_R}$$

where the corresponding time scales are given by $\tau_R^{-1} = \tau_{on}^{-1} + \tau_{off}^{-1}$; $\tau_{on}^{-1} = f\alpha c_0 k_{on}$; $\tau_{off}^{-1} = k_{off}$.

The peak concentration $c_{max}$, in some embodiments, is expressed in terms of the initial concentration in the well, $c_0$ and a pre-concentration factor, $\alpha$, such that $c_{max} = \alpha c_0$. Utilizing the present model for the peak concentration, $c_{max}$, as well as Eq.(1) for $\eta_{TE}$, yields $$\alpha = \frac{c_{max}}{c_0} = \frac{1}{c_0} \frac{N_a}{\sqrt{2\pi} A\sigma} = \sqrt{\frac{8}{\pi}} \frac{\eta_{TE} x_0}{w}$$

where $x_0$ is the position of the reacting surface. The corresponding solution which applies to times $0 \le t \le \tau_{ITP}$, and practically coincides with the exact numeric solution at $t = \tau_{ITP}$, is given by $$\frac{b(t)}{b_m} = \frac{\tau_R}{\tau_{on}}\left(1 - \exp\left(-\frac{t}{\tau_R}\right)\right)$$

where the time scale which governs the reaction rate may be rewritten as $$\tau_R = \frac{1}{k_{on}(f\alpha c_0 + K_d)}$$

with the reaction constant $K_d = k_{off}/k_{on}$ setting a typical concentration scale in our problem. The latter introduces a natural scale which separates the low concentration and high concentration regimes, governed by the off-rate and by the on-rate, respectively. It is worth noting that owing to the fact that in our setup the diffusion time, $\tau_d$, is at least four orders of magnitude smaller than the reaction time, $\tau_R$, the corresponding surface reactions are not diffusion limited.

In another embodiment, $\tau_{ITP}$ corresponds to the duration in which the focused sample overlaps with the reactive surface. The total assay time is however typically much longer, and is dominated by the electromigration time of the interface from the TE well to the reaction site, $\tau_{tot} = x_0/V_{ITP}$. The exact governing equation for the case of reaction under standard flow conditions (no ITP) is identical to Eq.(9), except with the preconcentration factor set to unity, $f\alpha = 1$, indicating that the concentration of the analyte in contact with the surface remains $c_0$. To obtain a fair comparison between the two reaction modalities, we compare the final normalized number of hybridized probes, $b/b_m$, after an identical total time $\tau_{tot}$. In the standard, pressure driven flow case, the arrival time of the target molecules to the reacting surface is negligible, and $\tau_{tot}$, plays the role of the total reaction time. The ratio of these signals, indicating the enhancement due to ITP is given by $$R(c_0) = f\alpha \frac{k_{off} + c_0 k_{on}}{k_{off} + f\alpha c_0 k_{on}} \frac{1 - \exp(-(k_{off} + f\alpha c_0 k_{on})\tau_{ITP})}{1 - \exp(-(k_{off} + c_0 k_{on})\tau_{tot})}.$$

In another embodiment, at low concentrations, we obtain an upper bound on the signal ratio given by $$R \to f\alpha \frac{1 - \exp(-k_{off}\tau_{ITP})}{1 - \exp(-k_{off}\tau_{tot})} \sim f\alpha \frac{\tau_{ITP}}{\tau_{tot}}$$

where $\tau_{ITP}$, $\tau_{eff}$, $\tau_{tot}$ $\tau_{off}$ is assumed, and expanded the exponents up to the first order in their arguments. At high concentrations, set by the corresponding equilibrium constant, the ratio decays to a lower bound of $R \to 1$ representing the fact that at sufficiently high concentrations (with respect to $K_d$), which saturate the sensor, no significant gain is obtained from ITP. Clearly, Eq.(16) shows that the typical time needed for the standard flow method to match the ITP method. Specifically, for times greater than, $\tau_{tot} > f\alpha\tau_{ITP}$, and low concentrations, the standard flow method becomes superior to the ITP method.

Figure 2:
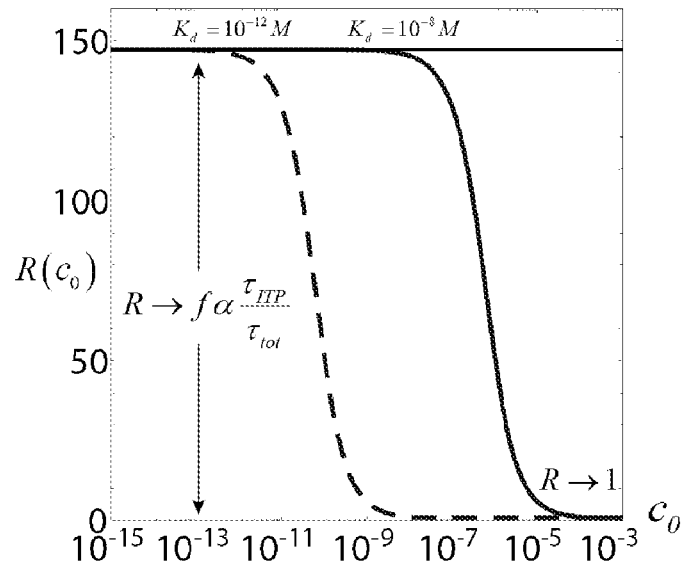
FIG. 2 Analytical model results showing the ratio of surface hybridization fractions between ITP-based and standard flow hybridization, as a function of the initial target concentration.

FIG. 2 presents this ratio of signals, as a function of the initial concentration at the well, for two typical values of $K_d$. Here the total reaction time for the standard flow-through conditions is taken as $\tau_{tot} = 180$ s, whereas the ITP reaction time is taken as $\tau_{tot} = 4$ s. Assuming the surface is located 2 cm from the TE reservoir, to obtain $\alpha = 22,000$, and $f\alpha$ 7000. Hence, while ITP increases the effective concentration over the surface by a factor 7000, it spends only ¼5 of the time over the surface, and thus the total enhancement, at low concentrations, is of the order $R \sim 150$.

The present model and FIG. 1 reveal that ITP-based reactions are particularly advantageous at low concentration, where $c_0$ $K_d$. In fact, Eq.(1.14) implies that in the regime $$\frac{K_d}{f\alpha} c_0 K_d,$$

sample focusing shifts the characteristic time scale from off-rate dominated to on-rate dominated resulting in both faster reactions and a higher fraction of reacted sites. At lower concentrations, $$c_0 \frac{K_d}{f\alpha},$$

both the standard and the ITP-based reactions are governed by the off rate. Nevertheless, the gain from ITP is maintained as the number of target molecules delivered to the surface is higher by a factor of $f\alpha$. In contrast, at higher concentrations, $c_0$ $K_d$, the gain from ITP quickly diminishes. This is because, even without focusing, and given the allocated reaction time, the initial concentration is sufficient to saturate the sensor. Thus, while ITP still enables faster reaction rates, they are no longer important when the allowed assay time is much longer than both reaction times.

1. FIG. 2 Analytical model results showing the ratio of surface hybridization fractions between ITP-based and standard flow hybridization, as a function of the initial target concentration. For illustration of the physical behavior, we present the results for two different $k_{on}$ values, $10^2$ and $10^6$ $M^{-1}$ $sec^{-1}$ (resulting in different $K_d$ values). ITP-based reactions provide significant signal enhancement in the regime $c_0$ $K_d$, where, in addition to a higher total number of target molecules delivered, sample focusing accelerates the characteristic reaction rate from $\tau_{off} = 1/k_{eff}$ to $\tau_{on} = 1/(f \alpha c_0 k_{on})$. At higher concentrations the initial concentration (without focusing) is sufficient to saturate the sensor, and no significant gain is obtained from ITP. Here $k_{eff} = 10^6$ $sec^1$, $\alpha = 2.2 \cdot 10^4$, the total reaction time for the standard flow-through conditions is $\tau_{tot} = 180$ s, and the ITP reaction time is $$\tau_{ITP} = \frac{\ell + w}{V_{ITP}} = 4\ s\ (\ell = 10^{-4}\ m; w = 10^{-4}\ m; V_{ITP} = 0.5 \cdot 10^{-4}\ m/s).$$

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

The common methods for patterning of capture probes on a surface require multiple well controlled chemical steps, and strongly depend on the substrate used. The majority of surface chemistries are performed by silanol chemistries. Prerequisite for grafting of silane is the availability of surface hydroxyls groups, which can readily create covalent bonds with such silanes. Silicon substrates, whose wide spread use originates from the semiconductor industry, has thus gained popularity as a substrate for immobilization of biomolecules, owing to its high density of surface hydroxyls. Unfortunately, silicon surfaces are inherently conducting, and thus are incompatible with electrokinetic assays in which high electric fields are used.

Nonconductive substrates, such as glass, PDMS, and plastics are suitable for electrokinetic assays, but have comparatively lower density of free surface hydroxyls. Obtaining high quality and repeatable patterning on such surface is thus far more challenging. Furthermore, enclosing finite length, well define, functionalized surfaces within microfluidic channels is a challenging task, as the majority of microfabrication bonding techniques (e.g. plasma treatment, thermal bonding) are destructive to organics. Lastly, microfluidic channels containing a functionalized surface can be used only once, and must be replaced between experiments. While this is acceptable and even required for diagnostic products, in a laboratory setting it results in long turnaround time per experiment, and decreased reproducibility.

To overcome these difficulties we designed a microfluidic chip in which reaction surfaces are formed by streptavidin-coated paramagnetic beads, immobilized at desired sites by an external magnetic field. The beads are prelabeled with capture-probes (e.g. biotinilated oligonucleotides, or biotinilated antibodies), eliminating the need for surface modifications, and enables reusability of the chip. As illustrated schematically in FIG. 4 and experimentally in FIG. 5, our microfluidic chip includes a 5 μm deep "trench" of dimensions 100 μm×30 μm, in which magnetic beads are concentrated and trapped creating a uniform and well defined surface.

Figure 3A:
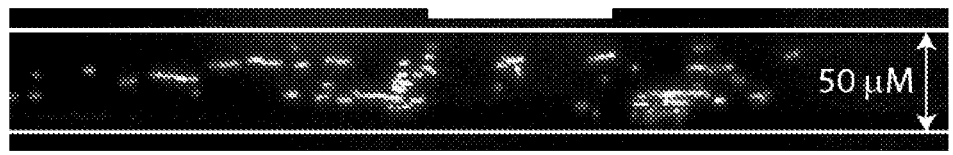
FIGS. 3a-b. Raw fluorescence images of 2.8 µm magnetic beads immobilized in a microchannel by an external cylindrical NdFeB magnet (⅛"×⅜" grade N52) (3a) beads trapped in a standard flat bottom micro-channel. The beads are successfully immobilized, but create a non-uniform and non-repeatable distribution. (3b) The same magnet is used to capture the same beads within a microfluidic trench, creating a uniform and well defined surface.
Figure 3B:

FIGS. 3a and 3b present experimental images of captured magnetic beads in a standard flat channel and in the trench design, respectively. Without the trench, while beads can be held in place, they are randomly and uncontrollably scattered within a long region of the channel.

Furthermore, it was currently found that beads held in this configuration are often displaced or removed upon applying an electric field. In contrast, the trench design confines the beads to a well defined region, creating reaction spot which is convenient to read to analyze. Using this configuration, we were able to apply electric fields as high as 300 V/cm, without any interruption to the beads' location.

Experimental Setup

An SU8 mold was fabricated at Stanford Microfluidic Foundry (Stanford University, CA, http://www.stanford.edu/group/foundry/) using standard lithography. A two layer design was used: the first layer was spun to 20 μm in thickness and a mylar mask was used to define a 50 μm wide, 50 mm long straight channel. The second layer was spun to 5 μm and was used to define the 30 μm wide×100 μm long bead capturing trench, located at the center of the channel. Using the mold, microfluidic chips were fabricated in house from PDMS, using a cross linker to monomer ratio of 1:10, and using standard protocols. Importantly, before baking, the PDMS was spun to a thickness of approximately 300 μm using a commercial spincoater (Larurell WS-650Mz-23NPP, North Wales, Pa.). The PDMS thickness dictates the distance between the external magnet and the channel, and thus directly affect the magnetic force.

Images were obtained using an inverted epifluorescent microscope (Ti-U, Nikon, Tokyo, Japan) equipped with a metal halide light source (Intensilight, Nikon Japan), a 10× (NA=0.45, WD=4 mm) Nikon PlanApo objective and Chroma 49006 filter-cube (620/60 nm excitation, 700/75 nm emission and 660 nm dichroic mirror). Images were captured using a 16 bit, 2560×2160 pixel array CMOS camera (Neo, Andor, Belfast Ireland) cooled to −40 C. Images were taken before and after the hybridization process, using an exposure time of 100 ms. During the hybridization process itself the light source was shuttered to prevent photobleaching of the immobilized probes. The camera was controlled using NIS Elements software (v.4.13, Nikon, Japan) and processed the images with MATLAB (R2011b, Mathworks, Natick, Mass.). All ITP experiments were performed using constant voltage (defined in each of the figures) using a high voltage sequencer (HVS3000D, Labsmith, Livermore, Calif.). Standard flow through hybridization experiments were performed using a water column connected to one of the channel's reservoirs.

Magnetic Beads and Labeling Protocol

A 2.8 μm paramagnetic beads (Dynal M280, Life Technologies, NY) were used, and applied a standard protocol, based on the manufacturer's instructions, to wash and label the beads. Briefly, 10 μl of the beads solution were mixed with a 90 μl of a 2× wash buffer containing 10 mM Tris, 20 mM HCl, 1 mM EDTA, and 2 M NACl. A Magnet was used to hold the beads in place, the fluid was discarded, and we repeated this process 4 time. We then mixed 10 μl of the washed beads with 10 μl of DI for a final salt concentration of 1 M, and added 1 µl of 20 µM probes. We incubated the beads for 10 min, washed them with a 1× wash buffer, and finally suspended them in 100 µl of DI. We estimate the final concentration of the labeled beads as 1 mg/ml, or $6E^7$ beads/ml.

Biotinilated Molecular Beacons and Target Sequences

The biotinilated molecular beacon probes were purchases from IDT (Coralville, Iowa). We designed a 22-mer probe sequence which is complementary to a preserved section of bacterial 16S rRNA. To the main probe sequence, we added 6 base-pairs on either side to form the molecular beacon stem. The 5' terminus was labeled with Cy5, and the 3' terminus was labeled with Black Hole Quencher 2 (BHQ2). Biotin label was placed on the quencher side of the stem, but as far as possible from its 3' terminus (Tan et al. *CHEMISTRY-WEINHEIM-EUROPEAN JOURNAL-*. 2000, 6, 1107-1111; and Schudel et al. ibid.). The final sequence is given by 5'-/Cy5/(CCGGAC{TCGTTTACRGCGTGGACTACCA}GT*CCGG) (SEQ ID NO: 1)/BHQ2, where T* denotes the biotin modification. Target nucleic acid, complementary to the probe sequence, TGGTAGTCCACGCYGTAAACGA (SEQ ID NO: 2), were purchased from Sigma-Aldrich (St. Louis, Mo.).

Bead Loading and Washing Process

For bead loading, we pipette 2 µL of the prelabeled beads (at a concentration of 6E7 beads/ml) into the West reservoir filled with 18 µL of LE solution. We place a cylindrical NdFeB magnet (⅛"×⅜" grade N52) on top of the channel, in direct contact with the PDMS, and created negative pressure of 60 cm H2O in the LE vial using a water column. Beads flow from the TE to LE reservoirs, and are captured in the trench under the magnetic field. Beads that are not captured in the trench are washed by the flow. We allow approximately 10 min for the beads to fill the trench, and subsequently flush the channel for 3 min with pure LE solution. To release the beads, we simply lift the magnet, and flush the channel with DI until all beads are removed.

Isotachophoresis Assay

For all experiments, the leading electrolyte (LE) was composed of 100 mM HCl and 200 mM bistris, and 1% 1.3 MDa poly(vinylpyrrolidone) (PVP). The trailing electrolyte (TE) was composed of 10 mM tricine and 20 mM bistris. We used a high ionic strength LE to maximize the focusing rate of species. PVP was used in the LE for suppression of electroosmotic flow (EOF). The TE concentration was chosen such that it provides sufficient buffering and repeatability, while also promoting focusing rate. Tricine, bistris, and PVP were obtained from Sigma-Aldrich (St. Louis, Mo.). HCl was obtained from Merck (Darmstadt, Germany) All buffer stock solutions were prepared in 20 mL glass bottles and kept at room temperature.

Once the beads-based surface has been established (see "beads loading" section), we cleaned the TE reservoir with DI, and filled it with 18 µl of TE solution and 2 µl of the target sequences (various concentration). For ITP experiments, we applied 1000 V across the channel for 1 min, then switched to 200 V and allowed 2 min for the ITP interface to pass the reaction site. For standard hybridization experiments we applied negative pressure of 60 cm H2O to the LE reservoir, and allowed 3 min of hybridization.

Results

Figure 5A:
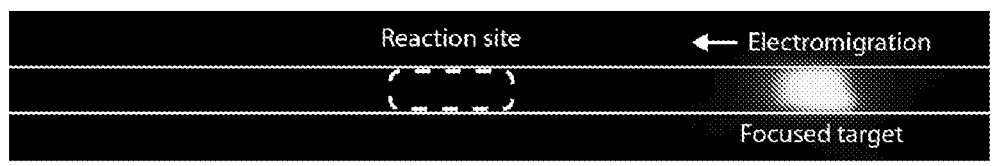
FIGS. 5a-c. Raw fluorescence images showing an experimental demonstration of ITP-based surface hybridization. (5a) Fluorescent DNA oligonucleotides are focused at the ITP interface and electromigrates toward the reaction zone composed of immobilized magnetic beads functionalized with complementary DNA probes (here still invisible). (5b) The ITP interface passes over the reaction zone allowing rapid hybridization of complementary strands. (5c) The ITP interface leaves the reaction zone, carrying unhybridized free targets, leaving the surface in a clean buffer environment.
Figure 5B:
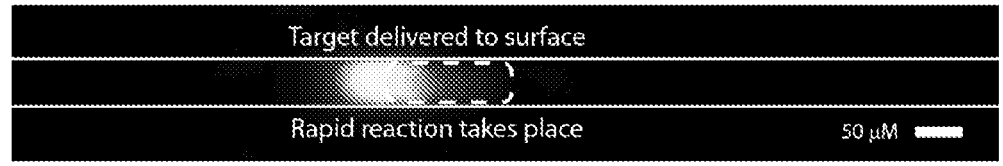
Figure 5C:
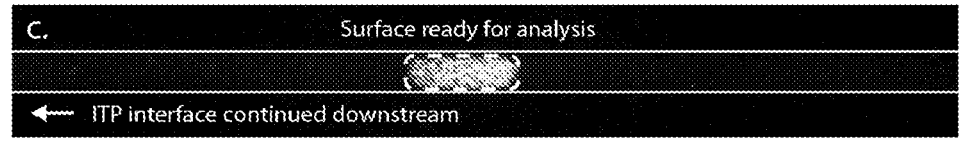

FIG. 5 presents a sequence of raw fluorescence images of ITP-based surface hybridization using 100 nM of target. Here, for illustrative purposes only, we have also labeled the target sequence such that the ITP interface is visible during its electormigraiton. As the ITP interface passes over the beads, rapid hybridization takes place causing enhanced fluoresce of the surface. At the applied voltage, the ITP interface transverses the surface in 4 s. However, as descried in the theory section, despite the short time, the high local concentration results in significant hybridization of the targets to the probes Importantly, after the short hybridization time, the ITP interface continues to electromigrate downstream in a well defined zone, carrying along remaining unhybridized targets or other contaminants. This serves an inherent 'wash' step, which leaves the sensor area submerged in a clean buffer environment with excellent optical access and low background noise. This constitutes a one-step react-and-wash assay which can be performed in a simple channel and does not require flow control elements or moving parts.

Figure 6A:
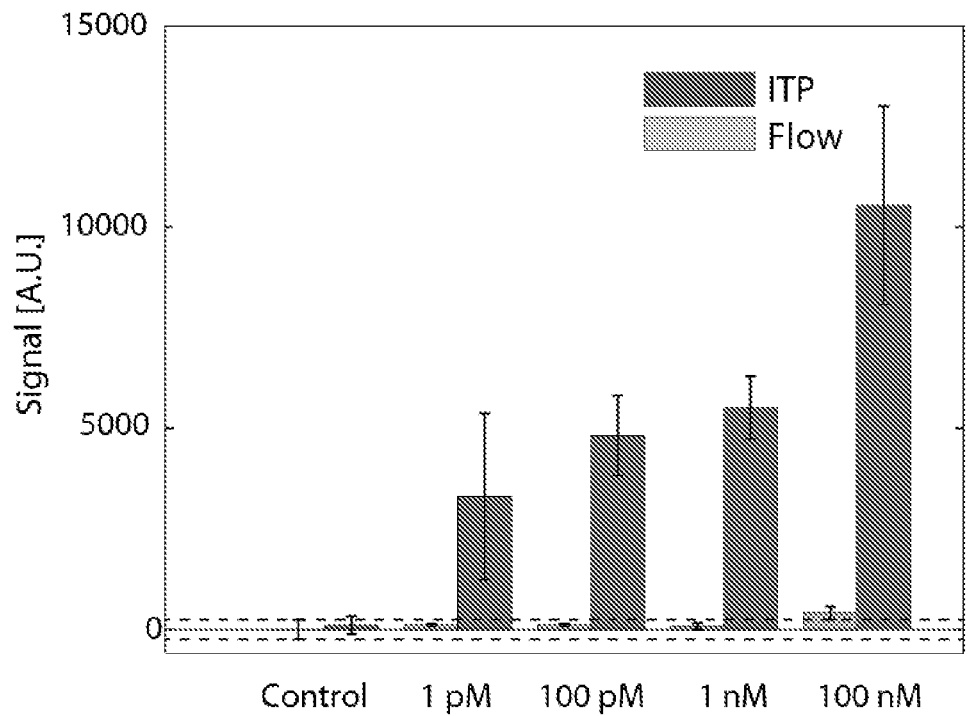
FIGS. 6a-b. (6a) Experimental results comparing ITP-based hybridization with standard flow through hybridization for initial concentrations between 1 pM to 100 nM. In both hybridization techniques the total assay time was 3 min. Each measurement corresponds to the difference in the average fluorescence intensity between a post- and pre-hybridization image, across a 80×20 pixels square at the center or the reactive surface. The height of each bar represents the average of at least 3 realizations (with 6 realizations for the standard flow control case, 7 repeats for all ITP experiments), with range bars representing 95% confidence on the mean. The dashed horizontal lines correspond to the range bars of the standard flow control case, and denote the confidence interface on the baseline. Results show a 30 fold increase in signal at concentration of 100 nM. At lower concentrations, the improved signal in ITP is clearly evident, though direct estimation of the improvement in signal is difficult since the standard hybridization cases did not result in significant signal above the baseline. Using ITP hybridization, we obtain a LoD of 1 pM in the ITP case, compared to 100 nM in the standard flow case. (6b) Kinetic experiment, measuring the signal as a function of time for the case of a standard pressure driven flow reaction, using a high, 1 µM, target concentration. Based on this measurement, we estimate the on-rate of the reaction $6 \cdot 10^3$ $M^{-1}s^{-1}$.

FIG. 6 presents a quantitative comparison of ITP-based surface hybridization with standard flow-through hybridization at initial concentration of 1 pM, 100 pM, 1 nM, and 100 nM. For each hybridization scheme we also performed a control case which followed the exact hybridization protocol, except with no sample in the reservoir. We performed the ITP assay by applying 1000 V across the channel for 1 min, then 200 V for 2 min, which results in the ITP interface arriving at the reactive surface after 3 min. For consistency in comparison of the results, we thus allowed exactly 3 min of flow in the standard hybridization case before imaging the surface.

For each experiment, regardless of the hybridization scheme, we subtract a background image (taken in LE solution, before hybridization begins) from the final data image. In several control experiments, we observed an average decrease in signal of 4% (ranging between 1 and 10%). We attribute this to small but finite photobleaching of the immobilized molecular beacons, and have thus performed an additional number of control experiments (6 in total) to better characterize this baseline. As it is most reasonable to assume that all experiments undergo similar photobleaching, the data in FIG. 6 is thus corrected, and presents the increase in signal above this reduced baseline value. This correction has essentially no effect on the ITP-based result, but slightly increases the flow based hybridization results. The horizontal dashed lines in FIG. 6 represent a 95% confidence interval on the value of this baseline.

Across all concentrations, we observed significant improvement in signal when using ITP-based hybridization. At concentrations of 1 pM, 100 pM, and 1 nM, the signal from flow-based hybridization is very low, within the margins of the baseline, and thus does not allow for quantitative comparison with the ITP-based hybridization values. However, based on comparison of the 100 nM hybridization data, we obtain a 30-fold improvement in signal in the case of ITP based hybridization. As discussed in the theory section, signal improvement in our setup strongly depends on the reaction constants. At low concentration, the upper bound for this value is 150-fold improvement. While we had measured the on-rate value, it is difficult to directly measure the off rate for this system. We can thus report only a qualitative, but not quantitative agreement with the model.

Furthermore, results show an LoD of less than 1 pM for ITP-based hybridization, compared with an LoD of 100 nM for the standard flow case. These results for standard flow are consistent with experiments on biotinilated surface molecular beacons, recently reported by Schudel et al. The authors reported a 10 nM LoD after a 1 hr hybridization time, and showed that the limiting step in their assay was beacon-oligo hybridization.

Figure 6B:
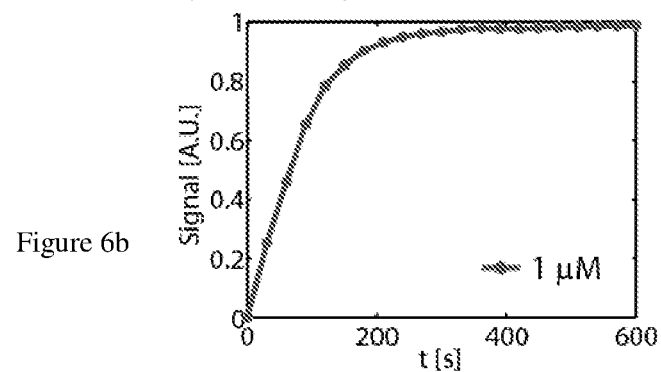
Figure 7A:
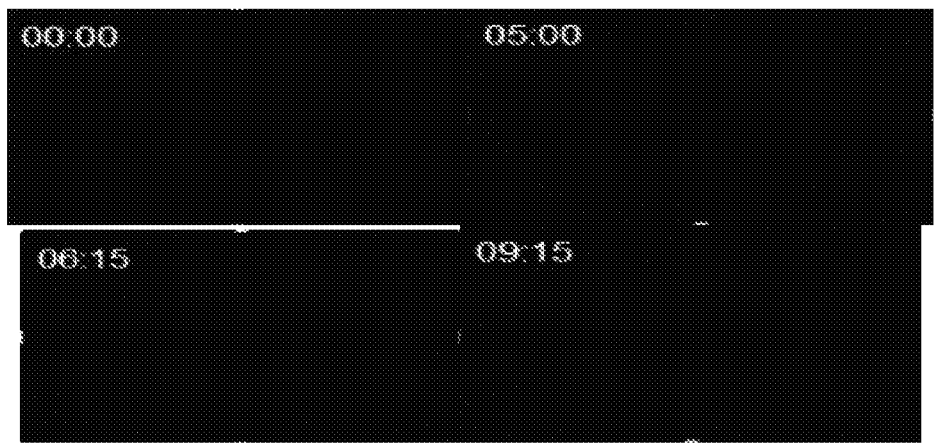
FIGS. 7a-b. Demonstration of accelerated surface reaction on a paper-based device. A nitrocellulose membrane is functionalized with immobilized molecular beacons. (7a) a DNA sample is delivered to the reaction site using standard lateral flow. Notably, reaction is slow and no signal is observed. (7b) ITP focusing is applied to the same initial DNA concentration. As the focused sample passes over the reaction site, reaction is accelerated, and clear signal is observed.
Figure 7B:
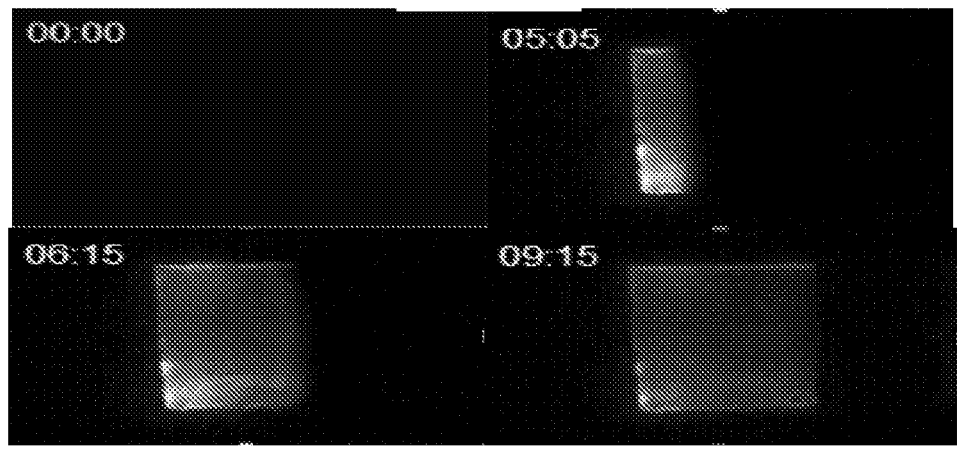

It was estimated the on-rate of the surface hybridization as $6 \cdot 10^3$ $M^{-1}s^{-1}$, based on an independent kinetic measurement we performed on the surface using standard pressure driven flow, but with a high concentration, 1 μM, target (see FIG. 6b). Thus, the characteristic reaction time for standard flow hybridization, even at a high concentration of 100 nM, is $\tau_R \sim (6 \cdot 10^3 \cdot 10^{-7})^{-1} = 1.6 \cdot 10^3$ s, which is equivalent to nearly 30 min. At lower concentrations, this rate is further decreased. Consistent with the experimental results, it is thus expected that during the 3 min allowed for this assay, the increase in signal will be minor. In contrast, in ITP, for the same initial concentration of 100 nM, the effective concentration at the interface will be approximately 700 μM (assuming f α=7000). The reaction time will thus be of the order $\tau_R \sim (6 \cdot 10^3 \cdot 7 \cdot 10^{-4})^{-1}$ 0.25 s. The ITP interface, moving here with a velocity of approximately 50 μm/s, transverses the surface in approximately 4 s—sufficient time for complete hybridization. At lower concentrations, the reaction rate decreases proportionally, but as results show, the gain in signal due to focusing is significant down to concentrations as low as 1 pM.

Conclusions

A new device and method for improving the sensitivity of surface sensors using ITP is presented. ITP was used to focus target molecules and deliver a highly concentrated sample to the reaction site, and thus accelerate reaction kinetics. Throughout the process, the sample is confined to the LE-TE interface and thus transverses the surface as a finite 'packet'. We have demonstrated that this results in an inherent wash step, in which any unreacted species or other contaminants continue electromigrating downstream.

The analytical model we developed enables direct prediction of the gains obtained by ITP-based reactions, as a function of the basic physical parameters in the system, and provides insight on the design and optimization of such assays Importantly, the model shows that the typical gain in surface-signal is far lower than the fold increase in sample concentration. This can be attributed to two main reasons: (i) the surface senses the average analyte concentration and not the peak concentration; and (ii) the total reaction time in the ITP-based assay is far shorter than in the standard flow-through experiment. Nevertheless, very significant gains of 30-fold in signal and a LoD of 1 pM be obtained, as we have demonstrated.

It was demonstrated that magnetic beads based surfaces are highly convenient for developing surface-based reaction assays in the lab settings. The ability to reuse each chip, while avoiding surface chemistry, was highly valuable in obtaining high turnaround time in experiments. The design of a trench in the channel for capturing the beads is crucial if well-defined and confined surfaces are desired.

Thus presented herein is a proof of principle experiments on DNA hybridization with molecular beacons, as this system is relatively easy to control and monitor.

What is claimed is:

1. A method of accelerating a surface-based reaction, the method comprising the following consecutive steps:
    (a) providing a microfluidic channel comprising at least one reaction surface comprising a groove, said groove comprising one or more probes immobilized thereto;
    (b) providing a sample comprising an analyte and focusing said analyte by isotachophoresis (ITP) at an ITP interface, thereby obtaining a focused analyte;
    (c) delivering said focused analyte to said one or more probes immobilized to said groove for hybridization by electro-migrating the ITP interface downstream and obtaining a hybridized analyte and an unhybridized analyte; and washing out consisting of hybridized analyte immobilized at the reaction surface and electro-migrating of the ITP interface further downstream from said reaction surface, carrying along said unhybridized analyte, a contaminant, or both;
    thereby accelerating a surface-based reaction.

2. The method of claim 1, wherein said delivering is selected from transversing said reaction surface, substantially modulating the electric field on top of the reaction surface for a pre-determined period of time, or applying counterflow on top of the reaction surface.

3. The method of claim 1, wherein said one or more probes is selected from a nucleic acid molecule, peptide nucleic acid, peptide, protein or antibody.

4. The method of claim 1, wherein said one or more probes comprises a label selected from the group consisting of fluorescently labeled, chemiluminescently labeled, radioactively labeled, and colorimetrically labeled.

5. The method of claim 1, wherein said channel has a height of 100 nm-1 mm.

6. The method of claim 1, further comprising performing analysis of the reaction to provide information on the hybridized analyte.

7. The method of claim 1, wherein said analyte, said hybridized analyte, said unhybridized analyte or any combination thereof is selected from an amino acid molecule, a nucleic acid molecule, a metabolite, a food additive, a drug constituent, a toxin, a pathogen, a heavy metal, a virus, a single celled organism, and a hormone.

8. The method of claim 1, wherein said sample is derived from patient specimen, said analyte, said hybridized analyte, said unhybridized analyte or any combination thereof is a marker for a disease or a clinical state of a subject, and wherein said one or more probes is capable of binding to said marker.

9. The method of claim 1, wherein said at least one reaction surface is coupled to a magnetic field generator, and wherein said one or more probes is bound to a paramagnetic bead thereby immobilizing said one or more probes to said reaction surface.

10. The method of claim 9, wherein said groove is a trench in said at least one reaction surface.

* * * * *